(12) United States Patent
Tohmeh

(10) Patent No.: US 8,506,598 B1
(45) Date of Patent: Aug. 13, 2013

(54) ANCHORS FOR SPINAL FIXATION AND CORRECTING SPINAL DEFORMITY

(75) Inventor: Antoine G. Tohmeh, Spokane, WA (US)

(73) Assignee: NuVasive, Inc., San Diego, CA (US)

( * ) Notice: Subject to any disclaimer, the term of this patent is extended or adjusted under 35 U.S.C. 154(b) by 39 days.

(21) Appl. No.: 12/803,510

(22) Filed: Jun. 28, 2010

Related U.S. Application Data

(60) Provisional application No. 61/220,679, filed on Jun. 26, 2009.

(51) Int. Cl.
*A61B 17/70* (2006.01)

(52) U.S. Cl.
USPC ............... 606/264; 606/267; 606/272

(58) Field of Classification Search
USPC .................................. 606/246–278
See application file for complete search history.

(56) References Cited

U.S. PATENT DOCUMENTS

| | | | |
|---|---|---|---|
| 5,002,542 A * | 3/1991 | Frigg | 606/264 |
| 5,047,029 A | 9/1991 | Aebi | |
| 5,196,013 A | 3/1993 | Harms et al. | |
| 5,209,752 A * | 5/1993 | Ashman et al. | 606/278 |
| 5,380,323 A | 1/1995 | Howland | |
| 5,575,791 A | 11/1996 | Lin | |
| 5,584,831 A | 12/1996 | McKay | |
| 5,741,255 A | 4/1998 | Krag | |
| 5,938,663 A | 8/1999 | Petreto | |
| 5,976,135 A | 11/1999 | Sherman et al. | |
| 6,083,226 A | 7/2000 | Fiz | |
| 6,106,526 A | 8/2000 | Harms et al. | |
| 6,123,706 A | 9/2000 | Lange | |
| 6,179,838 B1 | 1/2001 | Fiz | |
| 6,183,473 B1 | 2/2001 | Ashman | |
| 6,187,005 B1 | 2/2001 | Brace | |
| 6,210,413 B1 | 4/2001 | Justis | |
| 6,231,575 B1 | 5/2001 | Krag | |
| 6,248,105 B1 | 6/2001 | Martin | |
| 6,402,749 B1 | 6/2002 | Ashman | |
| 6,471,703 B1 | 10/2002 | Ashman | |
| 6,520,962 B1 * | 2/2003 | Taylor et al. | 606/278 |
| 6,626,906 B1 | 9/2003 | Young | |
| 6,648,887 B2 | 11/2003 | Ashman | |
| 6,685,705 B1 * | 2/2004 | Taylor | 606/278 |
| 6,802,844 B2 | 10/2004 | Ferree | |
| 6,872,209 B2 | 3/2005 | Morrison | |
| 7,066,939 B2 | 6/2006 | Taylor | |
| 7,083,622 B2 * | 8/2006 | Simonson | 606/279 |
| 7,211,087 B2 | 5/2007 | Young | |
| 2007/0270810 A1 | 11/2007 | Sanders | |
| 2008/0051780 A1 | 2/2008 | Vaidya et al. | |

FOREIGN PATENT DOCUMENTS

| | | |
|---|---|---|
| CA | 2045502 | 5/1991 |
| WO | 2006/029373 | 3/2006 |
| WO | 2008/013892 | 1/2008 |

* cited by examiner

*Primary Examiner* — Eduardo C Robert
*Assistant Examiner* — James Palmer
(74) *Attorney, Agent, or Firm* — Jonathan Spangler; Rory Schermerhorn

(57) ABSTRACT

A posted anchor and connector-based system including a splined shank headless anchor, various width adjustable connectors for use in open or minimally invasive thoracolumbar spine surgery. The connectors have a high degree of coronal, vertical, as well as sagittal adaptability. In one example, each plane of motion is individually secured for maximum versatility.

13 Claims, 9 Drawing Sheets

ANCHORS FOR SPINAL FIXATION AND CORRECTING SPINAL DEFORMITY

CROSS-REFERENCE TO RELATED APPLICATIONS

This application is an non-provisional patent application claiming the benefit of priority from U.S. Provisional Patent Application Ser. No. 61/220,679, entitled "Pedicle Screw for Spinal Deformity" filed on Jun. 26, 2009, the entire contents of which is hereby expressly incorporated by reference into this disclosure as if set forth in its entirety herein.

FIELD

The present invention relates to instrumentation associated with spinal fixation.

BACKGROUND

The human spine is comprised of a plurality of components (e.g. vertebral bodies, intervertebral discs, posterior bony structures) which collectively protect the spinal cord enable the normal physiological motions of flexion (bending forward), extension (bending backwards), lateral bending (bending side to side), and rotation (twisting). These normal physiologic motions may be impeded and/or pain generating when any of a number of conditions exists, including but not limited to disc degeneration, trauma, and deformity (e.g. scoliosis). Depending upon the condition, surgical intervention may be required to restore the normal physiologic function of the spine at the affected region. One form of surgical intervention involves fusing one or more levels within the spine. This is typically accomplished by performing a discectomy (removing part or all of an intervertebral disc), introducing a height-restoring implant into the disc space, and then immobilizing the adjacent vertebral bodies on either side of the intervertebral implant such that a bony bridge may form between the adjacent vertebral bodies to fuse that particular spinal segment. The step of immobilizing the vertebral bodies may be accomplished in many ways, including the use of pedicle screws (fixed axis or multi-axial) and rigid rods, wherein the pedicle screws are introduced into the pedicles associated with the respective vertebral bodies and the rigid rods are locked to each pedicle screw to prevent motion between the adjacent vertebral bodies.

In the lower lumbar spine, as well as spinal deformity at any level in the thoracolumbar spine, pedicle location in the coronal and axial planes varies between levels of vertebra. This creates significant difficulties in spinal instrumentation assembly. Several methods have been utilized to address these difficulties. First, surgeons bend the rods in the coronal plane. However, because the rods are simultaneously bent to create lordosis, this method tends to weaken the rods. Also, the bend is inconsistent and could not be used for minimally invasive surgery. Second, surgeons have tried rotating the rods into the coronal plane. However, this orients the curve intended for lordosis into the coronal plane, thus losing its lordotic shape and lowering the effectiveness of the spinal stabilization system. Third, surgeons have compromised the screw insertion path into the pedicle in order to facilitate assembly of the spinal stabilization system. Unfortunately, inserting the screws in a less than optimal position results in a less than optimal fixation and increases the probability the screw will loosen or even separate from the pedicle. Forth, surgeons have tried skipping levels to facilitate assembly. However, this method potentially compromises the stability of the spinal stabilization system and may increase the probability of rod breakage. Lastly, there are spinal fixation systems that are connector-based. However, these systems have various degrees of difficulty. For instance, the connector tends to rotate around the screws in the coronal plane when compression is applied.

The present invention is directed at overcoming, or at least improving upon, the disadvantages of the prior art.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The pedicle screw system disclosed herein boasts a variety of inventive features and components that warrant patent protection, both individually and in combination.

Using open or minimally invasive surgery, the spinal fixation system described herein is designed to treat spinal deformity at any level in the thoracolumbar spine, where pedicle location in the coronal and axial planes varies between levels. The pedicle screw assembly described herein utilizes a posted screw on which a connector assembly is mounted for receiving and rigidly holding a rod. The posted screw may be anchored in position prior to mounting of the connector, or the connector may be mounted to the screw prior to insertion. Mounting the connector to the screw after anchoring the screw in position can advantageously allow the screws to be placed (for various potential benefit, e.g. as a landmark for subsequent work, as a distraction platform, etc. . . . ) prior to completing work at the operative site (e.g. disc preparation, implant insertion, etc. . . . ) without inhibiting access to the operative site. Additionally, the screw assembly provides for a high degree of intraoperative axial, coronal, and sagittal adaptability. According to one example, movement in each plane of motion can be individually secured for maximum versatility. According to another example, a single step locking device may be used to lock movement in all planes of motion. The connector assemblies may come in various sizes to account for variability in patient anatomy and/or the extent of the deformity being corrected. According to a preferred use, at least two screw assemblies are anchored within the pedicles of at least two neighboring vertebrae. A connecting rod is positioned within the connector of each screw assembly and the rod is locked in position, thereby fixing the position of the screw assemblies relative to each other, and hence the position of the applicable vertebrae as well.

Figure 1:
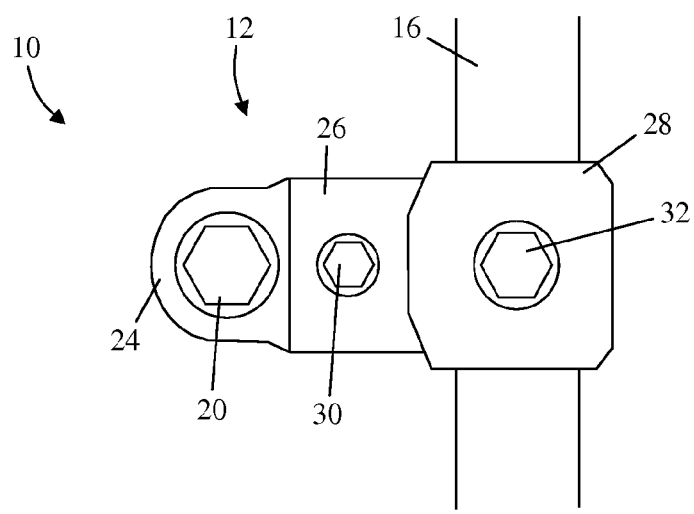
FIG. 1 is a top view of the screw assembly with a connector assembly and a rod, according to one example embodiment.
Figure 2:
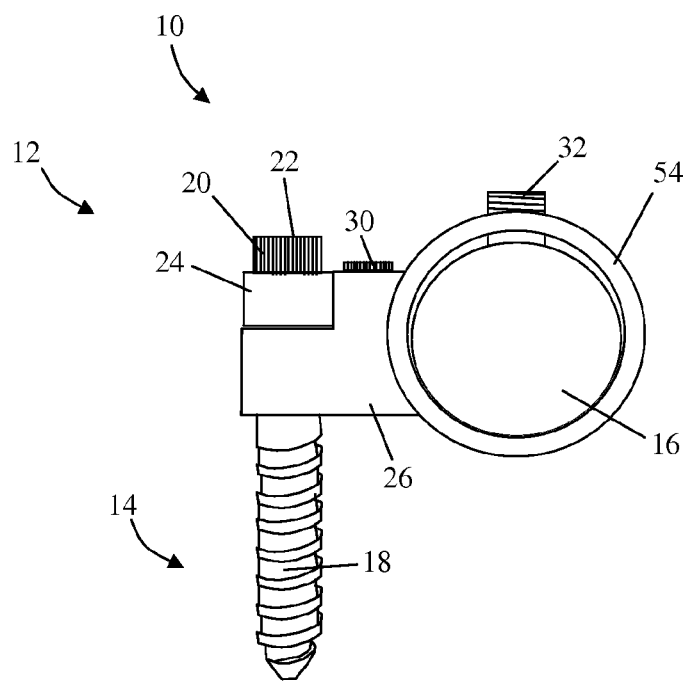
FIG. 2 is a side view of the screw assembly of FIG. 1.

Turning to FIGS. 1 and 2, an example of one embodiment of an anchor assembly 10 is illustrated. The anchor assembly 10 comprises a connector assembly 12 and a posted anchor 14. A rod 16 is shown in position within the connector assembly 12. The posted anchor 14 has an anchor portion 18 that is anchored to the bone anchor site (e.g. threaded through a vertebral pedicle and into a vertebral body) and a vertically-splined shank portion 20 which connects to the connector assembly 12. According to the embodiments shown, the anchor is a bone screw configured for implantation in a vertebral pedicle. Various other known anchors, e.g. hooks, staples, etc. . . . , could also adapted to include a splined shank 20 and mate with the connector assembly 12. The length of the anchor 14, including the length of either or both the anchor portion 18 and the vertically-splined shank portion 20, may be varied to accommodate the variability in patient anatomy and/or surgeon preference. For similar reason, the width of the anchor portion 18 may also be varied. Preferably, a plurality of variously sized anchors 14 are provided in a kit (together with connector assemblies 12 and rods 16, which may also be provided in various sizes) to permit intraoperative assessment and selection.

Figure 3:
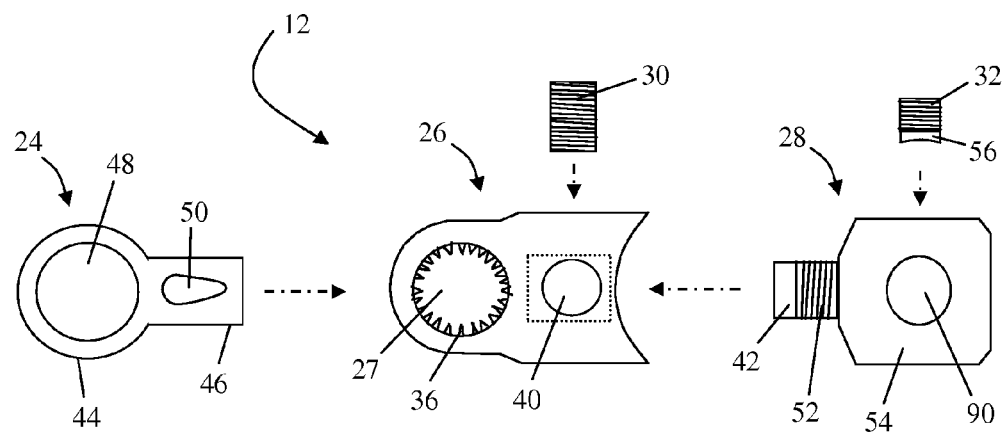
FIG. 3 is an exploded top view of the connector assembly of FIG. 1.
Figure 4:
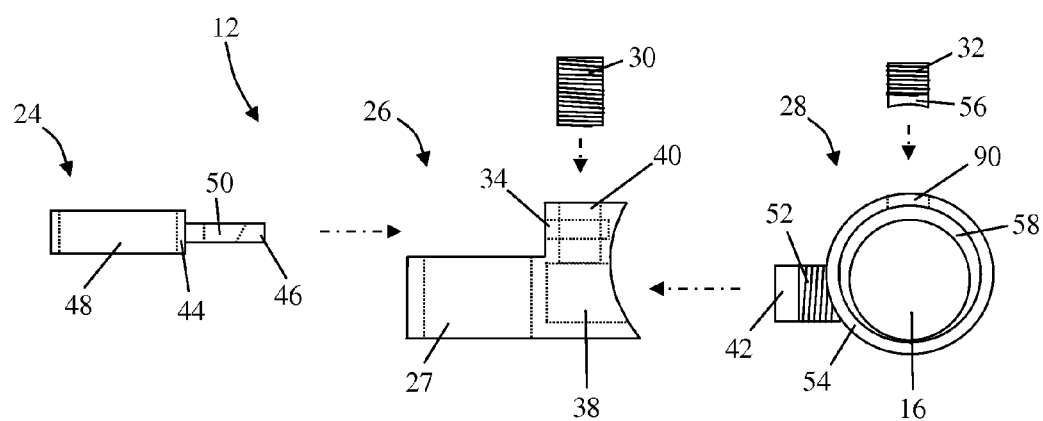
FIG. 4 is an exploded side view of the connector assembly of FIG. 1.
Figure 5:
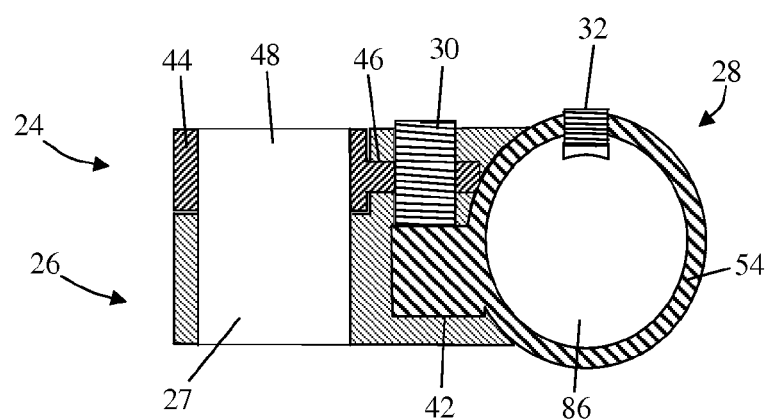
FIG. 5 is a cross section view of the connector assembly as shown in FIG. 2 without a rod and anchor.

According to one example, the connector assembly 12 includes a base 26, a receiver 28, a translation member 24, a connector locking set screw 30 and a rod locking set screw 32. To facilitate understanding of the connector assembly 12, FIGS. 3 and 4 show a top down and side exploded view of the connector assembly 12, respectively, and FIG. 5 shows a cross section view of the assembled connector assembly 12.

The base 26 has a vertical through bore 27 adapted to receive the splined shank 20 of the bone anchor 14. Within the through bore 27 are situated a plurality of engagement tines 36 adapted to cooperatively engage the vertical splines 22 on the shank 20. An inner diameter of the through bore 27, that is, the diameter measured at the tips of the tines 36 may be just larger than the outer diameter, that is, the diameter around the tips of the splines 22. Thus, the interface between the splined shank 20 and the through bore 27 is such that initially the through bore 27 may freely rotate around the shank 20, providing for coronal adjustment of the connector assembly 12. When the connector locking set screw 30 is tightened the translation member 24 and base move laterally toward the shank 20 such that some of the splines 22 of the shank 20 interdigitate with corresponding engagement tines 36, inhibiting coronal movement of the connector assembly. The height of the connector may also be adjusted along the shank until the connector locking set screw 30 is tightened beyond a necessary torque (which is less than the torque required to lock the receiver 28). As best appreciated in FIG. 4, offset from the through bore 27, the base includes a first cavity 34 opening in a the direction towards the through bore 27 and dimensioned to receive a flange 46 of the translation member. A second cavity 38 opening in the direction away from the through bore 27 and dimensioned to receive a projection 42 of the receiver 28 is provided below the first cavity. A receptacle 40 adapted to threadedly receive the connector locking set screw 30 opens to the upper surface of the base 26. The receptacle 40 transects the first cavity and opens into the second cavity 38. When the connector locking set screw 30 is tightened it passes into the second cavity 38 and frictionally engages the projection 42 to lock the position of the receiver 28 and inhibit sagittal movement.

The translating, member 24 has a body 44 and a flange 46. The body 44 has a through bore 48 adapted to slide over the splined shank 20 of the posted anchor 14. The through bore 48 may have tines (not shown) similar to the tines 36 in the base through bore 27 but in either case, the through bore 48 has an inner diameter just larger than the outer diameter of the splined shank portion 20, such that the splines 22 do not inhibit rotation of the translating member 24 around the shank 20 when unlocked. When the connector assembly 12 is assembled, the through bore 48 of the translating member 24 rests above the through bore 27 of the base 26 and the flange 46, which extends medially from the side of the body 44, is received within the first cavity 34 of the base 26. Contained within the flange 46 is an eccentric slot 50 that aligns with the receptacle 40 adapted to receive the connector locking set screw 30. Advancing the connector locking set screw 30 through the tapered eccentric slot 50 creates a medially directed force on the translating member 24 and base 26, which compress against the shank 20 to inhibit vertical travel and coronal movement of the connector assembly.

The receiver 28 has a projection 42 and a body 54. The projection 42 is dimensioned to fit within the second cavity 38 of the base 26 and may be partially threaded 52 or situated with an alternate non-threaded retention device (e.g. ridges, etc. . . . ). The non-threaded end may be provided with knurling or other surface features to increase friction with the connector locking set screw 30 (which may also be provided with knurling or other surface features where it engages the projection 42), which acts on the projection to inhibit sagittal movement. This turnbuckle like design provides for an unlimited rotation of the receiver 28 relative to the base, and thus for a large degree of sagittal adjustability. The body 54 has a rod channel 58 for receiving the rod therein. Although not required, according to one example, the diameter of the rod channel 58 is much larger than outer diameter of the rod 16 to facilitate passage of the rod therethough. A receptacle 90, adapted to threadedly receive the rod locking set screw 32 is situated in the top of the body 54 and opens into the channel 58. The rod locking set screw 32 may have a concave end 56 to match the contour of the rod 16. The rod locking set screw 32 may be threaded near the top and non-threaded near the concave end 56 and further adapted such that the non-threaded portion and the concave end 56 can spin freely relative to the threaded portion. This allows the surgeon better tighten the rod locking set screw 32 against the rod 16 and thus friction lock the connector assembly 12 to the rod 16.

Figure 6:
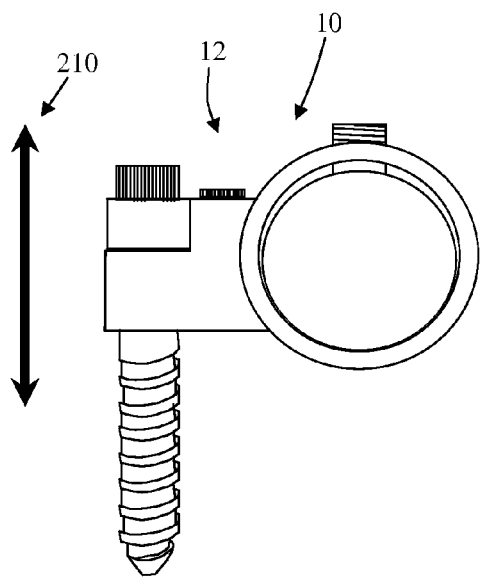
FIG. 6 is a side view that shows the axial translation adjustability of the connector assembly of FIG. 1.
Figure 7:
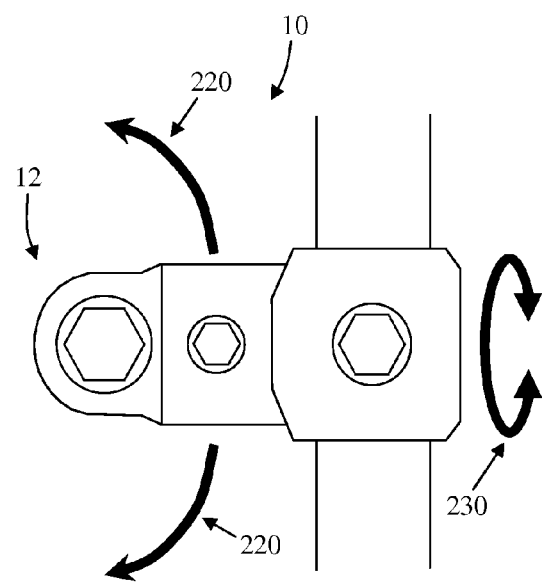
FIG. 7 is a top view that shows the coronal and sagittal angulation adjustability of the connector assembly of FIG. 2.
Figure 8:
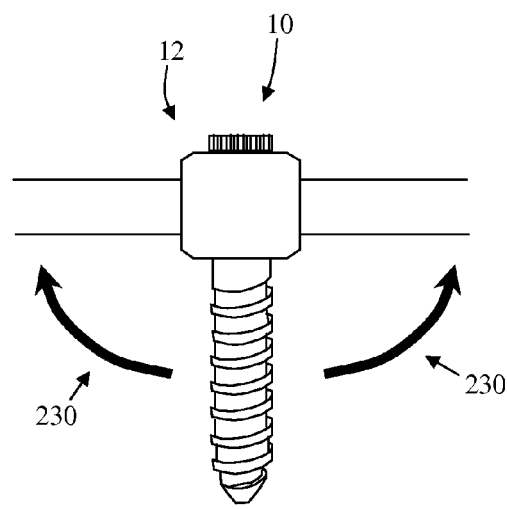
FIG. 8 is a medial view that shows the sagittal angulation adjustability of the connector assembly of FIG. 1.

According to a preferred embodiment, the connector assembly 12 is preassembled prior to surgery, with the locking set screws 30 and 32 loosely installed. To fix the spine using the anchor assembly, the surgeon first delivers the anchor 14 to the selected target site and implants the anchors the anchor portion 18 into the bone. Next, the preassembled connector assembly 12 is attached to the shank 20 by passing the through bores 27 and 48 over the shank 20. The connector assembly 12 can be rotated around the shank 20 until the desired coronal positioning is achieved. Likewise, the connector assembly 12 can be raised or lowered until the desired height or axial positioning is achieved. Partially tightening the connector locking set screw 30 will lock the connector assembly 12 to the anchor 14, preventing coronal and axial movement without yet limiting the sagittal movement of the receiver 28 which may still be adjusted to help facilitate insertion of the rod 16. Once the rod is inserted, the connector locking set screw 30 may be fully tightened to inhibit rotation of the receiver 28. FIGS. 6-8 illustrate the three planes of movement achievable with the screw assembly 8 described above. FIG. 6 illustrates the axial adjustability 210, achieved by sliding the base 26 and translation member 24 up and down along the splined shank 20. FIG. 7 shows the coronal adjustability 220 achieved by rotating the base and translation member 24 around then splined shank 20 and the sagittal adjustability achieved by rotating the receiver 28 relative to the base 26. FIG. 8 again depicts the sagittal adjustability achieved by rotating the receiver 28 relative to the base 26. While the spinal fixation system has been described with reference to a single anchor assembly 10, it will be appreciated that multiple anchor assemblies 10, including 2, 3, 4, or more anchor assemblies may be implanted in various levels of the spine to connect one or more rods over multiple vertebrae. It will also be appreciated that the spinal fixation system may be applied bilaterally.

Figure 9:
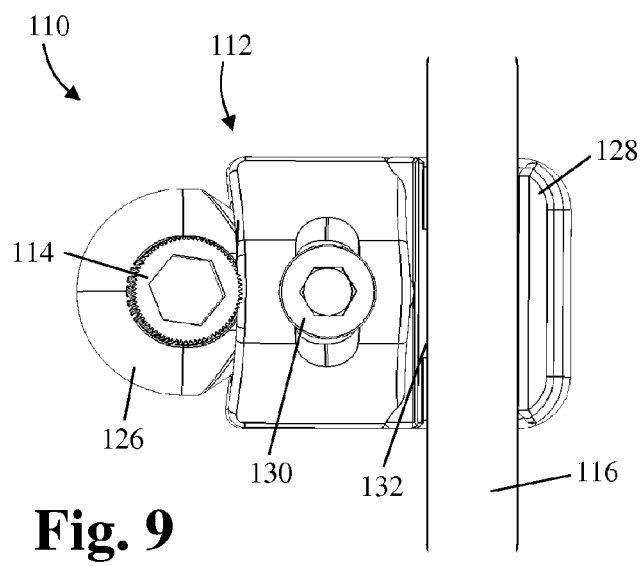
FIG. 9 is a top view of a screw assembly with a connector assembly and rod, according to another example embodiment.
Figure 10:
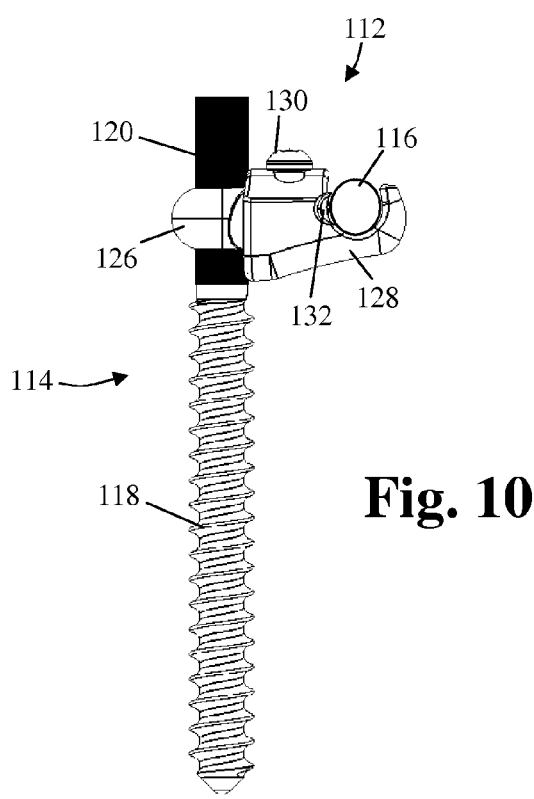
FIG. 10 is a side view of the screw assembly of FIG. 1.
Figure 11:
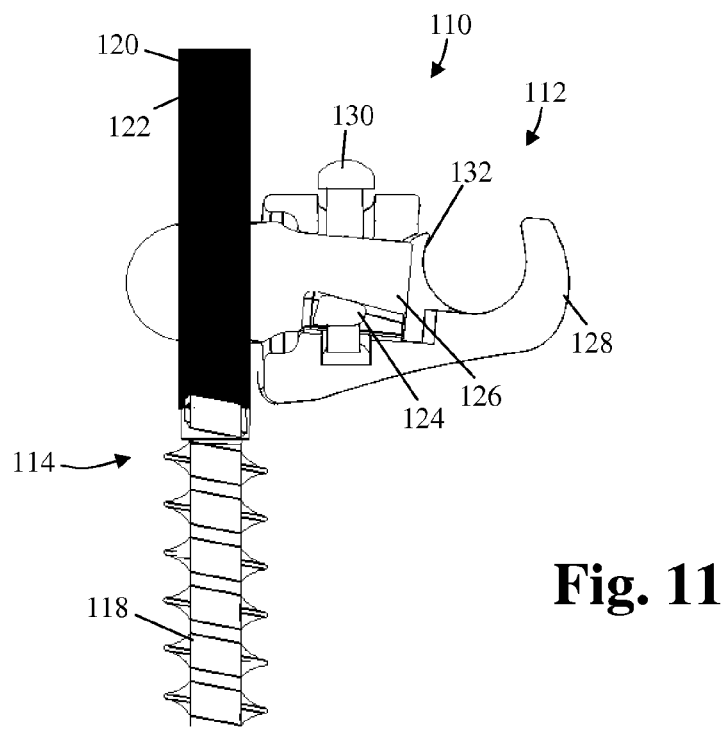
FIG. 11 is a cross section of the screw assembly as shown in FIG. 11.

With reference now to FIGS. 9-22, another example embodiment of an anchor assembly 110 is illustrated. Turning to FIGS. 9-11, the anchor assembly 110 comprises a connector assembly 112 and a posted anchor 114. A rod 116 is shown in position within the connector assembly 112. The posted anchor 114 has an anchor portion 118 that is anchored to the bone anchor site and a vertically-splined shank portion 120 which connects to the connector assembly 112. The anchor portion 118 illustrated is a bone screw configured for insertion through a vertebral pedicle and into a vertebral body. Various other known anchors, e.g. hooks, staples, etc. . . . , could also adapted to include a splined shank 120 and mate with the connector assembly 112. The length of the anchor 114, including the length of either or both the anchor portion 118 and the vertically-splined shank portion 120, may be varied to accommodate the variability in patient anatomy and/or surgeon preference. For similar reason, the width of the anchor portion 118 may also be varied. Preferably, a plurality of variously sized anchors 114 are provided in a kit (together with connector assemblies 112 and rods 116, which may also be provided in various sizes) to permit intraoperative assessment and selection.

Figure 12:
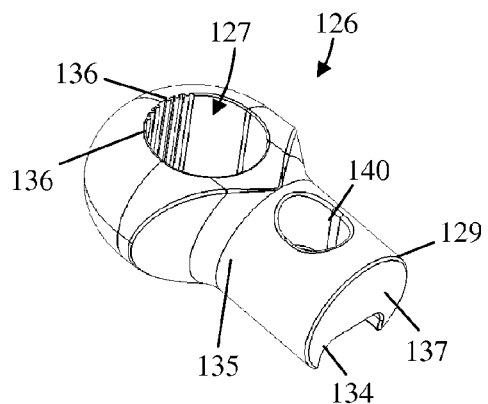
FIGS. 12 and 13 are side perspective and bottom perspective views, respectfully, of a base forming part of the connector assembly of FIG. 9.
Figure 13:
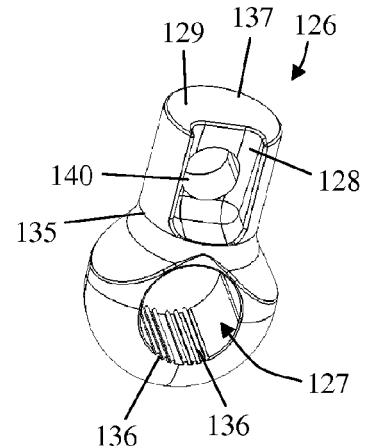
Figure 14:
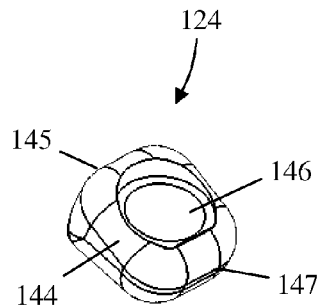
FIG. 14 is a perspective view of a translation member forming part of the connector assembly of FIG. 9.

According to this example, the connector assembly 112 includes a base 126, a receiver 128, a translation member 124, a connector screw 130, and a rod clamp 132. As shown in FIGS. 12-13, the base 126 has a vertical through bore 127 adapted to receive the splined shank 120 of the bone anchor 114. Along a lateral edge of the through bore 127 are situated a plurality of engagement tines 136 adapted to cooperatively engage the vertical splines 122 on the shank 120. An inner diameter of the through bore 127 (i.e. the diameter measured at the tips of the tines 136) may be just larger than the outer diameter (i.e. the diameter around the tips of the splines 122). Thus, the interface between the splined shank 120 and the through bore 127 is such that initially the through bore 127 may freely rotate around the shank 120, providing for coronal adjustment of the connector assembly 112. When the connector screw 130 is tightened the receiver 128 is forced laterally and presses on the shank 120 causing some of the splines of the shank 120 interdigitate with the corresponding engagement tines 136 on the base 126, inhibiting coronal movement of the connector assembly. The height of the connector assembly 112 may also be adjusted along the shank 120 until the connector screw 130 is tightened beyond a necessary torque. Offset and extending laterally from the through bore 127, the base 126 extends as a generally cylindrical body 129. Within the generally cylindrical body 129 is a cavity 134 dimensioned to slidably receive the translation member 124. The cavity 134 has a tapered profile such that the height of the cavity 134 at a lateral end 135 (closer to the through bore 127) is greater than the height at the open medial end 137 farther from the through bore 127. A receptacle 140 adapted to receive the connector screw 130 extends from the upper surface of the cylindrical body into the cavity 134. The receptacle 140 has an oblong cross section such that the receptacle 144 is longer along the axis of the cylindrical body (between the lateral and medial ends 135, 137) than it is wide. This allows the connector screw 130 to translate towards the through bore 127 (and hence the anchor 114) when engaged with the translating member 124.

The translating member 124 includes a body 144 enclosing an aperture 146 adapted to threadedly receive the connector screw 130. The body 144 is tapered to complement the taper of cavity 134. That is, the body has a height at a lateral end 145 that is greater than the height at the medial end 147. When the connector assembly 12 is assembled, the translating member 144 rests in the cavity 134. Advancing the connector screw 130 through the threaded receptacle 144 draws the translating member 124 upwards where the complementary taper of the translating member 124 and the cavity 134 (along with the oblong base receptacle 140) cause the translation member 124 to move laterally toward the through bore 127.

Figure 15:
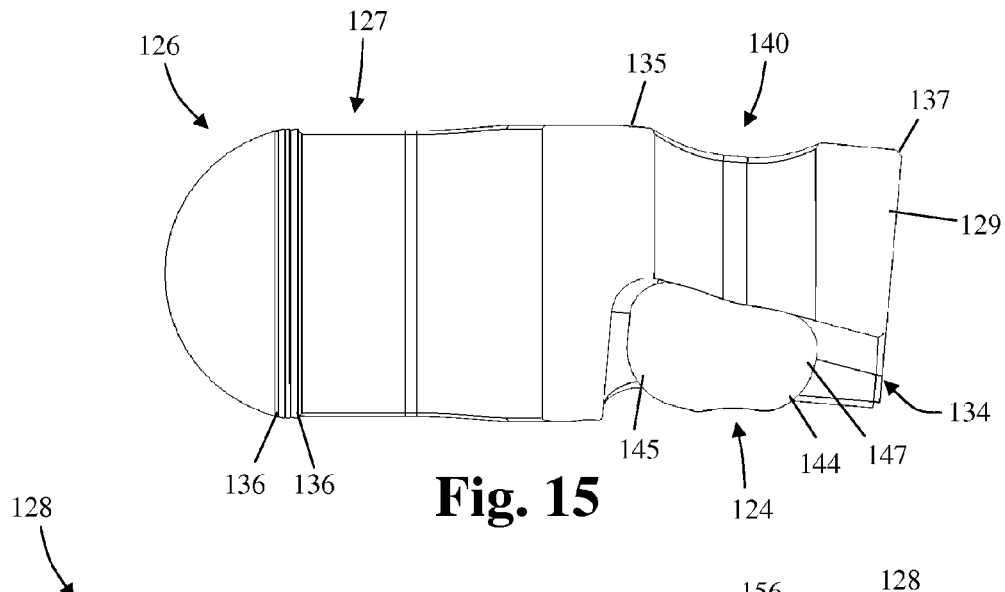
FIG. 15 is a side cross section view of the base of FIGS. 12-13 with the translation member of FIG. 14.
Figure 17:
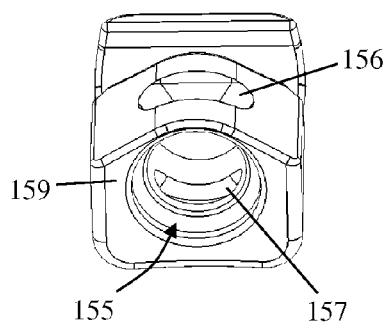
FIGS. 16 and 17 are top perspective and lateral perspective views, respectfully, of a receiver forming part of the connector assembly of FIG. 9.
Figure 16:
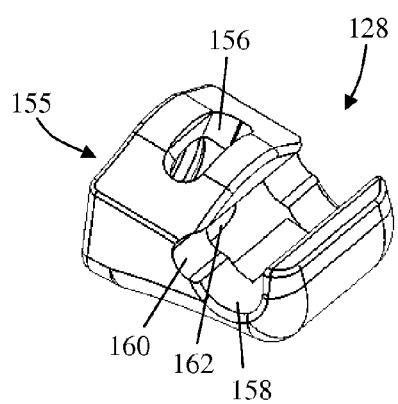
Figure 18:
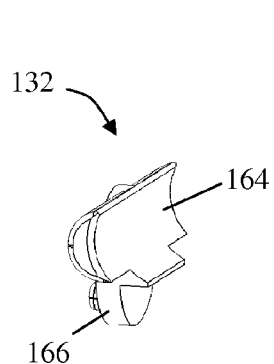
FIG. 18 is a side perspective view of a rod clamp forming part of the connector assembly of FIG. 9.
Figure 19:
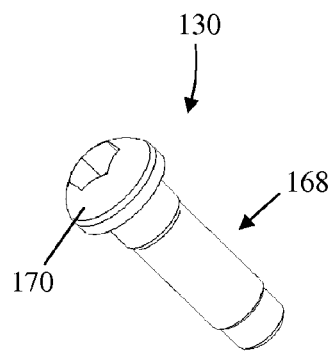
FIG. 19 is a side perspective view of a connector screw forming part of the connector assembly of FIG. 9.

With reference to FIGS. 15-16, the receiver 128 has a body 154 defining a generally cylindrical receptacle 155 opening at a lateral face 159 and dimensioned to receive the generally cylindrical body 129 of the base 126. Opposite the lateral face is a rod channel 158 including a rod clamp 132. Upper and lower slots 156, 157 in the body 154 open into the receptacle 155. The slots 156, 157 are oriented perpendicular to the axis of the cylindrical body 129 allowing the receiver 128 to rotate around cylindrical body 129 to provide sagittal adjustment without the connector screw 130 inhibiting the movement. The length of the slots 156, 157 may be varied to provide for the desired amount of sagittal adjustability. By way of example, the slots may be formed to provide approximately 60° of sagittal correction. The rod clamp 132 (FIG. 18) rests in a clamp groove 162 formed in the receiver body 154 such that a rod contacting surface 164 of the clamp 132 forms part of the rod channel 158. A pedestal 166 of the clamp 132 protrudes into the receptacle 155 from the rod channel 158 and rests in contact with the base 126.

Figure 20:
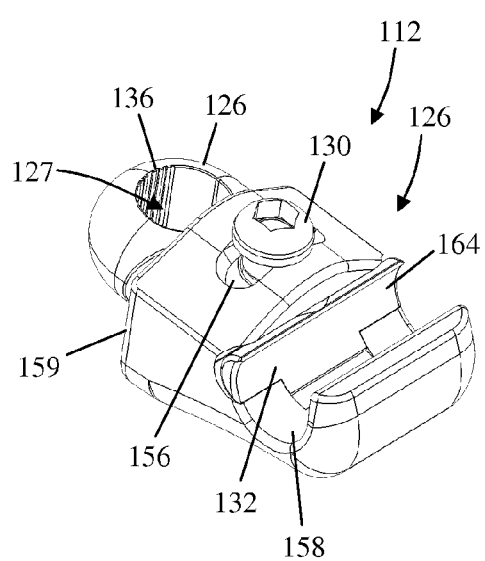
FIG. 20 is a side perspective view of the fully assembled connector assembly of FIG. 9.
Figure 21:
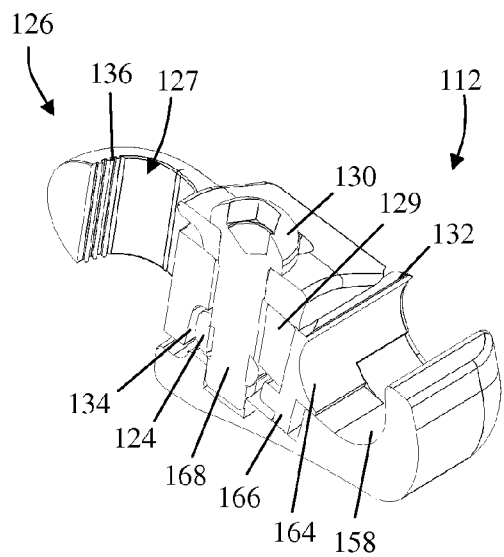
FIG. 21 is a cross section view of the of the fully assembled connector assembly of FIG. 20.

Turning to FIGS. 20-21, the connector assembly 112 is preferably provided preassembled with the connector screw 130 loosely engaged such that the assembly is in a fully unlocked orientation. When the connector assembly 112 is assembled, the cylindrical body 129 with the translation member 124 positioned in the cavity 134 is received in the receiver receptacle 155. The connector screw 130 traverses the upper slot 156 of the receiver, the oblong receptacle 140 of the base 126, and threads into the translation member 124. The rod clamp 132 is positioned in the receiver 128 as described above. When the threaded shaft 168 of the connector screw 130 is engaged to lock the connector assembly, the translation member 124 is forced toward the through bore 127, bringing the connector screw 130 and the receiver 128 with it. The connector screw 130 preferably passes completely through the translation member 124 and into the lower slot 157 to make an additional point of contact with the receiver 128 and provide for even compression. The clamp 132 is held in position by the base 126 and does not translate with the receiver 128. When the lateral face 159 of the receiver compresses against the anchor shank 120 the splines 122 engage with the tines 136. The compression of the receiver against the shank 120 inhibits axial translation of the connector assembly up and down the shank 120 (axial adjustments) and rotation around the shank (coronal adjustments). Additionally, the head 170 of the connector screw 130 frictionally engages the body 154 of the receiver 128 and inhibits rotation of the receiver 128 around the base (sagittal adjustments). As the receiver 128 translates toward the anchor shank 120 the rod 116 is captured between the outer rod channel wall (which translates with the rest of the receiver 128) and the rod clamp (which does not translate with the receiver 128).

Figure 22:
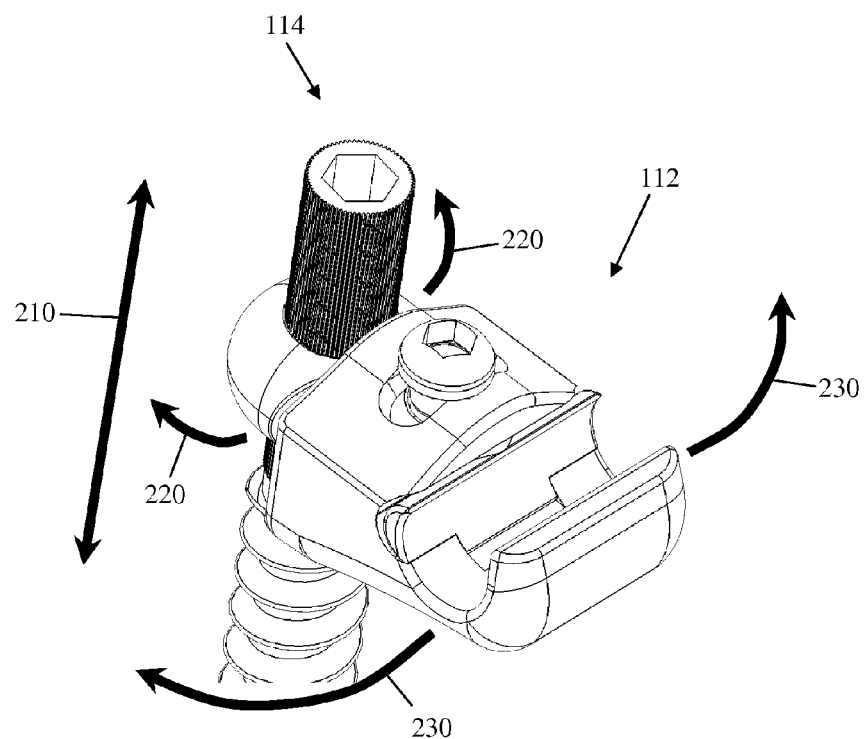
FIG. 22 is a side perspective view of the screw assembly of FIG. 9 depicting the axial, coronal, and sagittal adjustability achievable with the screw assembly.

In use, the preassembled connector assembly 112 is attached to a previously implanted shank 120 by passing the through bore 127 over the shank 120. The connector assembly 112 can be rotated around the shank 120 until the desired coronal positioning is achieved. Likewise, the connector assembly 112 can be raised or lowed until the desired height or axial positioning is achieved. Partially tightening the connector screw 130 to frictionally engage the splines 122 and tines 133 will lock the connector assembly 112 to the anchor 114, preventing coronal and axial movement. Sagittal movement may still be possible until the screw 130 is fully tightened, however, because the rod channel 158 is open at the top, additional sagittal adjustment may not be necessary just to facilitate rod insertion. FIG. 22 illustrates the three planes of movement achievable with the screw assembly 110. That is, the FIG. 22 illustrates the axial adjustability 210, achieved by sliding the base 126 up and down along the splined shank 120, the coronal adjustability 220 achieved by rotating the base 126 around then splined shank 120, and the sagittal adjustability achieved by rotating the receiver 128 relative to the base 126.

While the spinal fixation system has been described with reference to a single anchor assembly 110, it will be appreciated that multiple anchor assemblies 110, including 2, 3, 4, or more anchor assemblies may be implanted in various levels of the spine to connect one or more rods over multiple vertebrae. It will also be appreciated that the spinal fixation system may be applied bilaterally. Furthermore, various accessories may be provided with or modifications may be made to the anchor assemblies 10 and 110 without departing from the scope of the invention. By way of example, the anchors 14 and 114 may be cannulated such that they may be passed over a guide wire for minimally invasive surgery. During such a surgery it is contemplated that the splines 22 and 122 may be utilized to engage an instrument and provide countertorque. It is also contemplated to provide anchor extenders including a bottom portion that engages within a head of the anchor and an upper splined extension portion. This could eliminate the need, for example, for implanting extra long anchors and then having to cut the excess once the connectors are in place and the rod inserted, as the extension could simply be removed.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fixation anchor assembly for use with a spinal fixation rod, comprising:
   a bone anchor having a first longitudinal axis and comprising an anchor portion and post having a plurality of vertical splines,
   a connector that is adjustable relative to said bone anchor in each of axial, coronal, and sagittal directions, wherein the connector assembly has a base configured to couple to the bone anchor post, a receiver configured seat the spinal fixation rod, and a translation member, the base having a bore therethough, the bore having a second longitudinal axis that is parallel to the first longitudinal axis and a plurality of vertical splines arranged around at least a portion of the bore, the receiver having a rod passage opening in a top surface of the receiver and having a third longitudinal axis, the third longitudinal axis being transverse to the first longitudinal axis and second longitudinal axis, the translation member being situated in a cavity of the base and movable from a first position to a second position, wherein movement of the translation member to the second position locks said connector assembly in position relative to said bone anchor.

2. The spinal fixation anchor assembly of claim 1, wherein the base includes a cylindrical body adjacent the throughbore and extending laterally therefrom along a fourth longitudinal axis that is transverse to the first longitudinal axis, and wherein the receiver includes a cylindrical receptacle that receivers the cylindrical body such that the receiver can rotate about the base until the connector assembly is locked.

3. The spinal fixation anchor assembly of claim 2, wherein the translation member is a wedge and the base cavity has a taper complementary to the wedge.

4. The spinal fixation anchor assembly of claim 3, wherein the wedge has a threaded aperture passing from an upper surface to a lower surface of the wedge.

5. The spinal fixation anchor assembly of claim 4, including a screw threadably coupled to the wedge.

6. The spinal fixation anchor assembly of claim 5, wherein the receiver has an elongate slot opening into the receptacle and oriented perpendicular to the fourth longitudinal axis, and the cylindrical body has an elongate slot opening into the cavity and oriented parallel to the fourth longitudinal axis.

7. The spinal fixation anchor assembly of claim 6, wherein the screw passes through the receiver elongate slot and the cylindrical body elongate slot into the wedge.

8. The spinal fixation anchor assembly of claim 7, wherein rotating the screw in a first direction draws the wedge upwards against the tapered surface of the cavity which directs movement of the wedge and the screw laterally toward the bore.

9. The spinal fixation anchor assembly of claim 8, wherein movement of the wedge and screw laterally toward the bore causes the receiver to move laterally toward the bore.

10. The spinal fixation anchor assembly of claim 9, wherein the receiver includes a lower slot and the screw extends from the bottom surface of the wedge into the lower slot.

11. The spinal fixation anchor assembly of claim 9, wherein the movement of the receiver toward the bore causes the vertical splines on the anchor post to mate with the vertical splines in the bore to prevent rotation of the base around the anchor.

12. The spinal fixation anchor assembly of claim 9, wherein movement of the receiver toward the bore causes the receiver to frictionally engage the post to prevent vertical movement of the base along the post.

13. The spinal fixation anchor assembly of claim 9, wherein the receiver includes a rod clamp situated therein, the rod clamp forming a portion of the rod passage and wherein the rod clamp remains still when the receiver moves toward the bore such that the rod is squeezed between the rod clamp and the remainder of the rod passage.

\* \* \* \* \*